United States Patent
Wallin et al.

(10) Patent No.: US 10,912,913 B2
(45) Date of Patent: Feb. 9, 2021

(54) ANESTHESIA SYSTEM, A METHOD AND A COMPUTER-READABLE MEDIUM FOR ACTIVELY CONTROLLING OXYGEN DELIVERED TO A PATIENT

(71) Applicant: MAQUET CRITICAL CARE AB, Solna (SE)

(72) Inventors: Mats Wallin, Spånga (SE); Mario Loncar, Ekerö (SE); Christer Ahlmén, Sollentuna (SE); Pär Emtell, Vällingby (SE)

(73) Assignee: MAQUET CRITICAL CARE AB, Solna (SE)

( * ) Notice: Subject to any disclaimer, the term of this patent is extended or adjusted under 35 U.S.C. 154(b) by 858 days.

(21) Appl. No.: 14/427,843

(22) PCT Filed: Sep. 12, 2013

(86) PCT No.: PCT/EP2013/068962
§ 371 (c)(1),
(2) Date: Mar. 12, 2015

(87) PCT Pub. No.: WO2014/041103
PCT Pub. Date: Mar. 20, 2014

(65) Prior Publication Data
US 2015/0250976 A1    Sep. 10, 2015

Related U.S. Application Data

(60) Provisional application No. 61/700,053, filed on Sep. 12, 2012.

(51) Int. Cl.
*A61M 16/10* (2006.01)
*A61M 16/01* (2006.01)
(Continued)

(52) U.S. Cl.
CPC ...... *A61M 16/104* (2013.01); *A61M 16/0003* (2014.02); *A61M 16/0051* (2013.01);
(Continued)

(58) Field of Classification Search
CPC ... A61B 5/0205; A61B 5/02416; A61B 5/145; A61B 5/14539; A61M 16/00;
(Continued)

(56) References Cited

U.S. PATENT DOCUMENTS 5,365,922 A * 11/1994 Raemer ............... A61B 5/0833
128/202.22
6,213,120 B1 * 4/2001 Block ............... A61M 16/0075
128/204.21
(Continued)

FOREIGN PATENT DOCUMENTS

EP          0504725 A2      9/1992
EP          2363163 A1 *    9/2011  ............ A61M 16/12
WO    WO-2007/015197 A2    2/2007

*Primary Examiner* — Annette Dixon
(74) *Attorney, Agent, or Firm* — Fay Kaplun & Marcin, LLP

(57) ABSTRACT

An anesthesia system has a unit for measuring oxygen concentration delivered to a patient, a unit for sending an alarm to an operator if the measured oxygen concentration is below a first threshold value, and a unit for automatically increasing a setting of oxygen in a fresh gas setting, so that the oxygen concentration delivered to a patient is increased, if the measured oxygen concentration is below a second threshold value. The system allows for increased safety or a lowered fresh gas flow with a maintained safety level.

20 Claims, 5 Drawing Sheets

(51) Int. Cl.
*A61M 16/00* (2006.01)
*A61M 16/08* (2006.01)
*A61M 16/22* (2006.01)
*A61M 16/18* (2006.01)
*A61M 16/20* (2006.01)

(52) U.S. Cl.
CPC .......... *A61M 16/01* (2013.01); *A61M 16/024* (2017.08); *A61M 16/1005* (2014.02); *A61M 16/1015* (2014.02); *A61M 16/0891* (2014.02); *A61M 16/18* (2013.01); *A61M 16/205* (2014.02); *A61M 16/208* (2013.01); *A61M 16/22* (2013.01); *A61M 2016/1025* (2013.01); *A61M 2202/0007* (2013.01); *A61M 2202/0208* (2013.01); *A61M 2202/0241* (2013.01); *A61M 2202/0266* (2013.01); *A61M 2205/18* (2013.01); *A61M 2205/3334* (2013.01); *A61M 2205/502* (2013.01); *A61M 2205/52* (2013.01)

(58) Field of Classification Search
CPC .......... A61M 16/0045; A61M 16/0051; A61M 16/0063; A61M 16/01; A61M 16/0891; A61M 16/1015; A61M 16/107; A61M 16/12; A61M 16/122; A61M 16/125; A61M 16/18; A61M 16/209; A61M 16/22; A61M 2016/0027; A61M 2016/0039; A61M 2016/1025; A61M 2016/1035; A61M 2202/0208; A61M 2202/0241; A61M 2202/025; A61M 2202/0283; A61M 2202/0291; A61M 2205/18; A61M 2205/3368; A61M 2205/50; A61M 2205/505; A61M 2205/52; A61M 2205/581; A61M 2205/583; A61M 2230/005; A61M 2230/202; A61M 2230/205; A61M 2230/208; A61M 2230/43; A61M 2230/432; A61M 2230/435
USPC ............ 128/203.14, 204.18, 204.21, 204.23, 128/205.13, 205.23
See application file for complete search history.

(56) References Cited

U.S. PATENT DOCUMENTS

| | | | |
|---|---|---|---|
| 6,671,529 B2* | 12/2003 | Claure | A61M 16/0051 600/323 |
| 7,527,054 B2* | 5/2009 | Misholi | A61M 16/12 128/204.22 |
| 8,770,192 B2 | 7/2014 | Tham | |
| 2005/0109340 A1 | 5/2005 | Tehrani | |
| 2006/0266355 A1* | 11/2006 | Misholi | A61M 16/12 128/204.23 |
| 2008/0058612 A1* | 3/2008 | Ohyu | G06Q 50/22 600/300 |
| 2009/0241956 A1* | 10/2009 | Baker, Jr. | A61M 16/12 128/204.23 |
| 2009/0320836 A1* | 12/2009 | Baker, Jr. | A61M 16/125 128/203.14 |
| 2010/0175695 A1* | 7/2010 | Jamison | A61M 16/01 128/203.14 |
| 2010/0224191 A1* | 9/2010 | Dixon | A61B 5/14539 128/204.23 |
| 2010/0224192 A1* | 9/2010 | Dixon | A61B 5/02416 128/204.23 |
| 2012/0192956 A1* | 8/2012 | Weiszl | A61M 16/12 137/3 |

* cited by examiner

ANESTHESIA SYSTEM, A METHOD AND A COMPUTER-READABLE MEDIUM FOR ACTIVELY CONTROLLING OXYGEN DELIVERED TO A PATIENT

BACKGROUND OF THE INVENTION

Field of the Invention

This invention pertains in general to the field of inhalational anesthesia systems. More particularly, the invention relates to controlling oxygen delivered to a patient, who is fluidly connected to the system, in order to avoid hypoxia of the patient.

Description of Related Art

Low flow inhalational anesthesia is typically used of economical reasons for saving fresh gas and vaporized anesthetic agents (AA) used during anesthesia. However, leakage may occur, or depending on user settings, oxygen uptake by a patient may be larger than what is being supplied back to the patient and may thus lead to hypoxia, i.e. the patient receives an inadequate oxygen supply.

In the prior art, different safety features of a breathing apparatus in order to avoid hypoxia of a patient have been disclosed. The most common measure is an alarm if oxygen provided by the anesthesia system drops below a set alarm value. However, the operator has to take manual action and adjust settings of the system to increase supplied oxygen. If the operator is inattentive or bound by other clinical tasks, the alarm may pass unattended and hypoxia becomes a fact. This is undesired.

As an example, US2012/0174926 A1 discloses a system for preventing the delivery of hypoxic gases during respiratory support of a patient. A processor calculates a predicted oxygen concentration for user selected ventilation parameter values, and compares the predicted oxygen concentration to a predetermined minimal oxygen required threshold of the patient. The ventilation parameter value selected by the user is only taken into operation of the system if the system considers the predicted oxygen concentration to be not hypoxic. An alarm may be given to an operator and the operator can override the alarm. This system interferes with the user's actions and does not allow the user to act freely. Moreover, although an alarm is given to an operator and although the operator can override the alarm, there are no further safety features to reliably prevent hypoxia. Thus, it is possible to erroneously ignore or override an alarm and hypoxia may occur. Normal operator interaction is interfered with and thus the operator may be perceived as confusing by a user because of the ineffective safety features disclosed in US2012/0174926 A1.

Thus, there is a need for an anesthesia system, in which safety features are provided in order to more reliably prevent hypoxia, preferably without interfering with a user's normal interactions with the system.

Hence, an improved anesthesia system for preventing hypoxia would be advantageous. Furthermore, an improved anesthesia system would be advantageous and in particular an anesthesia system allowing for increased flexibility, cost-effectiveness and/or increased safety towards patient hypoxia would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an anesthesia system, a method and a computer-readable medium according to the appended patent claims.

According to aspects of the invention, an anesthesia system, a method and a computer-readable medium for controlling oxygen concentration delivered to the patient in order to avoid hypoxia are disclosed.

An anesthesia system is provided that detects low inspired O2 concentration (FiO2) and automatically adjust the fresh gas flow and the oxygen (O2) concentration, preferably to predefined fixed FiO2 levels.

This is preferably done only if the user of some reason is non-responsive to warnings or alarms indicating the low FiO2 condition.

Thus, the user is given an opportunity to mitigate low FiO2 conditions before the automatic safety operation of the system delivers an increased, non-hypoxic, O2 amount to the patient to mitigate or avoid hypoxia.

Alternatively, or in addition, to an attempt to increase the FiO2 level, the system may perform an oxygen safety flush, without user initiation, for a predetermined amount of time to increase FiO2 quickly.

The user is preferably informed of the safety procedures to increase FiO2, such as by messages on a display of the system. Hence, the user may take note of the actions taken and that there might be a condition needing further attention of the user.

According to an aspect of the invention, an anesthesia system with hypoxia guard is provided. The system comprises a unit for measuring inspired oxygen delivered to a patient fluidly connected to the system. The system also comprises a control unit for triggering an alarm if the measured inspired oxygen is below a first threshold value. The control unit is configured to set the system to a safety mode if the measured inspired oxygen is below a second threshold value. The second threshold value is lower than the first threshold value, thus avoiding interference with a low Oxygen alarm. A safety gas mixture is provided to the patient at a predefined configuration in the safety mode for increasing the oxygen delivered to the patient. The control unit is configured to set the system to an operational safety mode for increasing the delivery of oxygen to the patient in such case. The control unit is further configured to activate the operational safety mode if the measured inspired oxygen value is below a second threshold value lower than the first threshold value, such as for at least a first predetermined time for mitigating or avoiding hypoxia of the patient.

The control unit may further be configured to set the anesthesia system, for automatically performing an oxygen flush, such as of a breathing circuit of the system. The oxygen flush is performed for a predetermined amount of time if the measured inspired oxygen value is below a third threshold value, such as for at least a second predetermined time, wherein the third threshold is lower than the second threshold value.

According to another aspect of the disclosure, a method of operating an anesthesia system with hypoxia guard is provided. The method comprises measuring inspired oxygen delivered to a patient fluidly connected to the system. The method also comprises triggering an alarm if the measured inspired oxygen is below a first threshold value. Furthermore, the method comprises setting the system to a safety mode if the measured inspired oxygen is below a second threshold value lower than the first threshold, wherein a safety gas mixture is provided to the patient at a predefined configuration in the safety mode for increasing the oxygen delivered to the patient. The method includes setting the system to the operational safety mode for increasing delivery of the oxygen to the patient when the measured inspired oxygen value is below the second threshold value lower than the first threshold value for at least a first predetermined time.

The method may further include setting the anesthesia system in an operational mode automatically performing an oxygen flush, such as of a breathing circuit of the system. The oxygen flush is performed for a predetermined amount of time if the measured inspired oxygen value is below a third threshold value, such as for at least a second predetermined time, wherein the third threshold is lower than the second threshold value.

According to a further aspect of the invention, a computer-readable medium having embodied thereon a computer program for processing by a computer of an anesthesia system is provided. The computer program comprises a code segment measuring inspired oxygen delivered to a patient fluidly connected to the system. The computer program further comprises a second code segment for triggering an alarm if the measured inspired oxygen is below a first threshold value. Moreover, the computer program comprises a third code segment for setting the system to a safety mode if the measured inspired oxygen is below a second threshold value lower than the first threshold, wherein a safety gas mixture is provided to the patient at a predefined configuration in the safety mode for increasing the oxygen delivered to the patient. The system is set to the operational safety mode for increasing delivery of said oxygen to said patient when said measured inspired oxygen value is below a second threshold value lower than said first threshold value, such as for at least a first predetermined time.

The computer program may include a code segment for setting the anesthesia system in an operational mode automatically performing an oxygen flush, such as of a breathing circuit of the system. The oxygen flush is performed for a predetermined amount of time if the measured inspired oxygen value is below a third threshold value, such as for at least a second predetermined time, wherein the third threshold is lower than the second threshold value.

Thus, fresh gas flow during normal operation can be reduced in a safe way and therefore the cost of operating the anesthesia system may be lowered and operational economy is improved. Furthermore, the patient is further protected from hypoxia and the operational and patient safety is increased when operating such system.

Further embodiments of the invention are defined in the dependent claims, wherein features for the second and subsequent aspects of the invention are as for the first aspect mutatis mutandis.

Some embodiments provide for an anesthesia system that detects low FiO2 and automatically adjust the fresh gas flow and the fresh gas O2 concentration to predefined fixed levels, preferably if the user is of some reason non-responsive to warnings or alarms indicating the low FiO2 condition.

Some embodiments of the invention provide for increased patient safety.

Some embodiments of the invention also provide for increased safety in case of machine failure.

Some embodiments of the invention also provide for that there is no interference with normal operator interaction and thus the operator is not confused by the safety features.

Some embodiments of the invention also enable the operator to remedy hazardous low levels of oxygen provided to a patient.

Some embodiments of the invention also provide for that the oxygen concentration delivered to a patient may be customized for different patients.

DESCRIPTION OF THE PREFERRED EMBODIMENTS

Specific embodiments of the invention will now be described with reference to the accompanying drawings. The following description focuses on an anesthesia system having a volume reflector system. However, it will be appreciated that the invention is not limited to this application but may be applied to many other systems including for example an open bellow system or a bellow driven anesthesia system. The skilled person is well acquainted with such systems, however only systems without any implementation of the present disclosure related to a Hypoxic Guard System.

Below is a function described for Active oxygen management including a Hypoxic Guard system in an anesthesia system. The Active O2 management is intended to handle different operational situations when an inspired O2 concentration (FiO2), i.e. the Fraction of inspired oxygen, can become very low and cause hypoxia in a ventilated patient.

Hypoxia (also known as hypoxiation) is a condition in which a patient's body is deprived of adequate oxygen supply. In the present context, hypoxia occurs in patients when an anesthesia system, i.e. an inhalational anesthesia system providing mechanical ventilation, provides breathing mixtures of gases with low oxygen content. A Hypoxic gas mix is a gas mix, which contains less oxygen than air, i.e. <21%.

A Hypoxic Guard System has the purpose to mitigate or prevent hypoxia of a patient and to ensure that suitable action is taken by the system in a desired operational context to increase the inspiratory oxygen to adequate non-hypoxic levels.

One of the operational situations is to make sure that the system has a safety action in case of a potential machine failure. A sub functionality that in particular is adequate to handle this case is referred to as function "LowFiO2safetyflush" or "Safety O2 Flush" in this document. This safety O2 flush is described in more detail below.

The other operational situation that may occur is a low FiO2 that needs to be handled. The sub functionality that handles this operational case is referred to as function "O2autoincrease" or "O2 Guard" in this description, and is also described in more detail below. It relates to issues that for instance can occur during Low Flow Anesthesia. O2autoincrease basically increases the oxygen delivered to the patient to prevent hypoxia in the patient. This is preferably only done as a safety feature in absence of a user action to increase a hypoxic FiO2 level to a non-hypoxic level.

Figure 1:
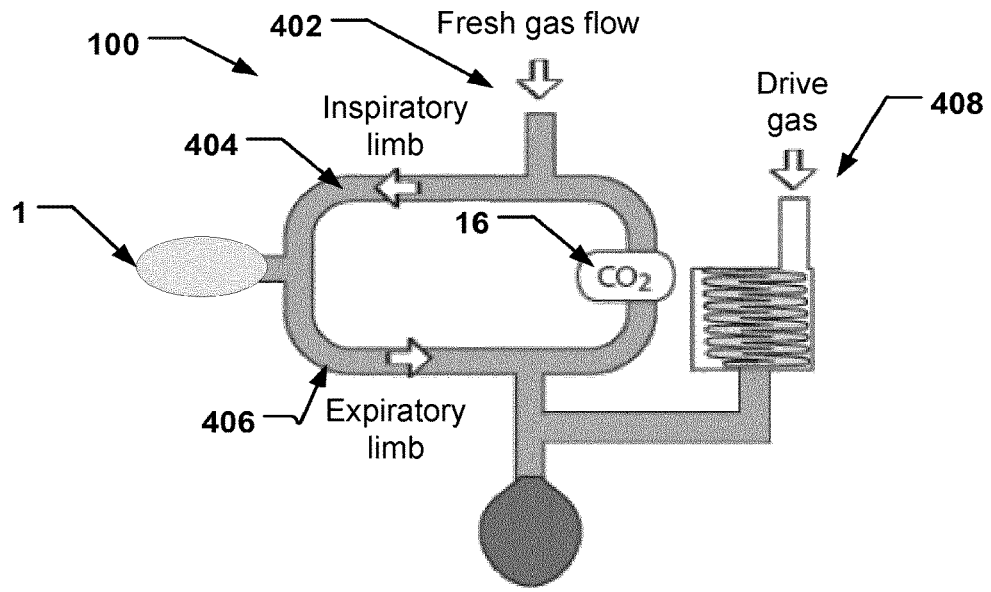
FIG. 1 is a schematic illustration of an anesthesia system, showing the dependencies of oxygen concentration delivery.

FIG. 1 is an illustration of an anesthesia system 100 implementing these safety features. FIG. 1 is rather schematically but sufficient for the skilled person to carry out the invention. A more detailed description is the anesthesia system 100 is nevertheless given below with reference to FIG. 6.

In FIG. 1 it is illustrated how the O2 concentration delivered to the patient has several dependencies. Fresh gas is delivered to an inspiratory limb 404 of a breathing circuit to a patient 1. Expiration is made via an expiratory limb 406. Rebreathing of such expired gases during subsequent inspiration is provided by removing CO2 in a CO2 absorber. Previously expired gas is collected in a Volume Reflector or bellows 408 and pushed back to the patient, while it can be mixed with fresh gas, in particular to replace Oxygen and anesthetic agent (AA) consumed by the patient. In such a "classic" anesthesia system 100, the O2 and AA concentration delivered to the patient 1 depend for instance on Fresh gas flow 402
Gas composition of the fresh gas flow 402
AA uptake of the patient 1
Oxygen uptake/Removed CO2 in a CO2 absorber 16
the Volume in the breathing circuit and the patient 1.

Examples of such anesthesia systems are for instance disclosed in WO 2007/071756A1, WO2009/062450A1 or WO2010/130290A1 of the same applicant as the present application. Another example can be found in of Werner, in which document an exchanger for open separation is disclosed. An example with a bellows can be also found in U.S. Pat. No. 4,989,597 (see FIG. 1), as well as in U.S. Pat. No. 4,127,121 of the University of Utah and in U.S. Pat. No. 5,537,992 of Bjoernstjerna et al. All these documents are incorporated herein by reference for all purposes.

In a traditional bellow driven anesthesia system the operator is given a visual feedback that the FG (fresh gas) flow is too low. If the patient consumes more oxygen than added, the volume in the breathing circuit will decrease, and after a while the bellow will be emptied prior to delivery of a complete tidal volume to the patient. The operator observes the bellow that is completely emptied and should normally increases the FG flow, but the patient may suffer from insufficient ventilation if the operator is unaware of the situation.

In some systems, such as a volume reflector system, there is no visual feedback from a bellow since there is none. In an "open bellow"/"Volume reflector" system, a sufficient breath can be delivered in spite of insufficient FG flow, but the breathing gas in the circuit will be diluted by the driving gas. In case air is used as driving gas, 21% O2, both the AA (anesthesia agent) and the O2 levels will degrade may resulting in hypoxia and potentially too low AA.

In both types of systems there is a need for increased safety. The safety features of the present disclosure may be implemented in both bellow or reflector anesthesia systems.

Figure 2:
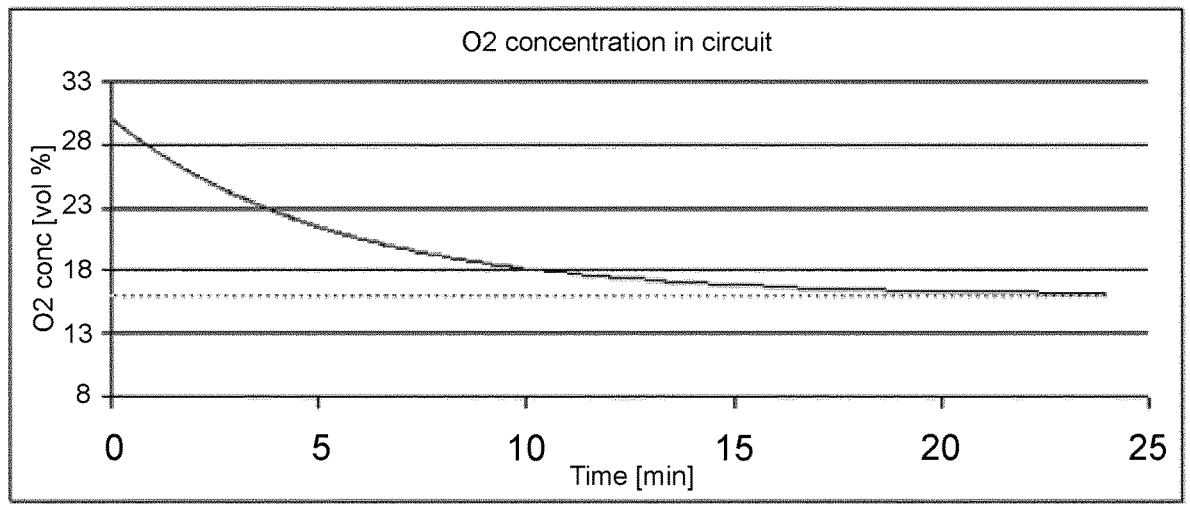
FIG. 2 is an illustration of how oxygen concentration may decrease over time in a breathing circuit when using low flow anesthesia in an anesthesia system.

Low flow anesthesia is typically used to save fresh gas and AA, and is therefore economically advantageous. In particular during low flow anesthesia, where a low fresh gas flow is used, the oxygen uptake by the patient may be larger than what is being supplied back to the breathing circuit, resulting in that the FiO2 decreases over time and may lead to hypoxia, see the example given in FIG. 2. It can be seen that the O2 concentration in the circuit decreases over time. The graph is based on the following simulation conditions: Fresh gas O2 concentration: 58%, Fresh gas flow: 0.5 l/min, Patient oxygen uptake: 250 ml/min, Circuit volume: 4 l. A gas leakage condition may also lead to such FiO2 decrease during low flow anesthesia.

In should be noted that in anesthesia systems, it is important to distinguish between set O2 concentration adjusted by the user and the O2 concentration delivered to the patient (FiO2). The O2 concentration set by the user together with the set gas flow determines how much volume (ml) of O2 is being delivered to the breathing circuit of the anesthesia system 100 as "fresh gas" (not the patient 1). In the circuit it is mixed with the recycled gas mix coming from the Volume reflector or bellows, resulting in a different O2 concentration that is delivered to the patient (FiO2).

Figure 3:
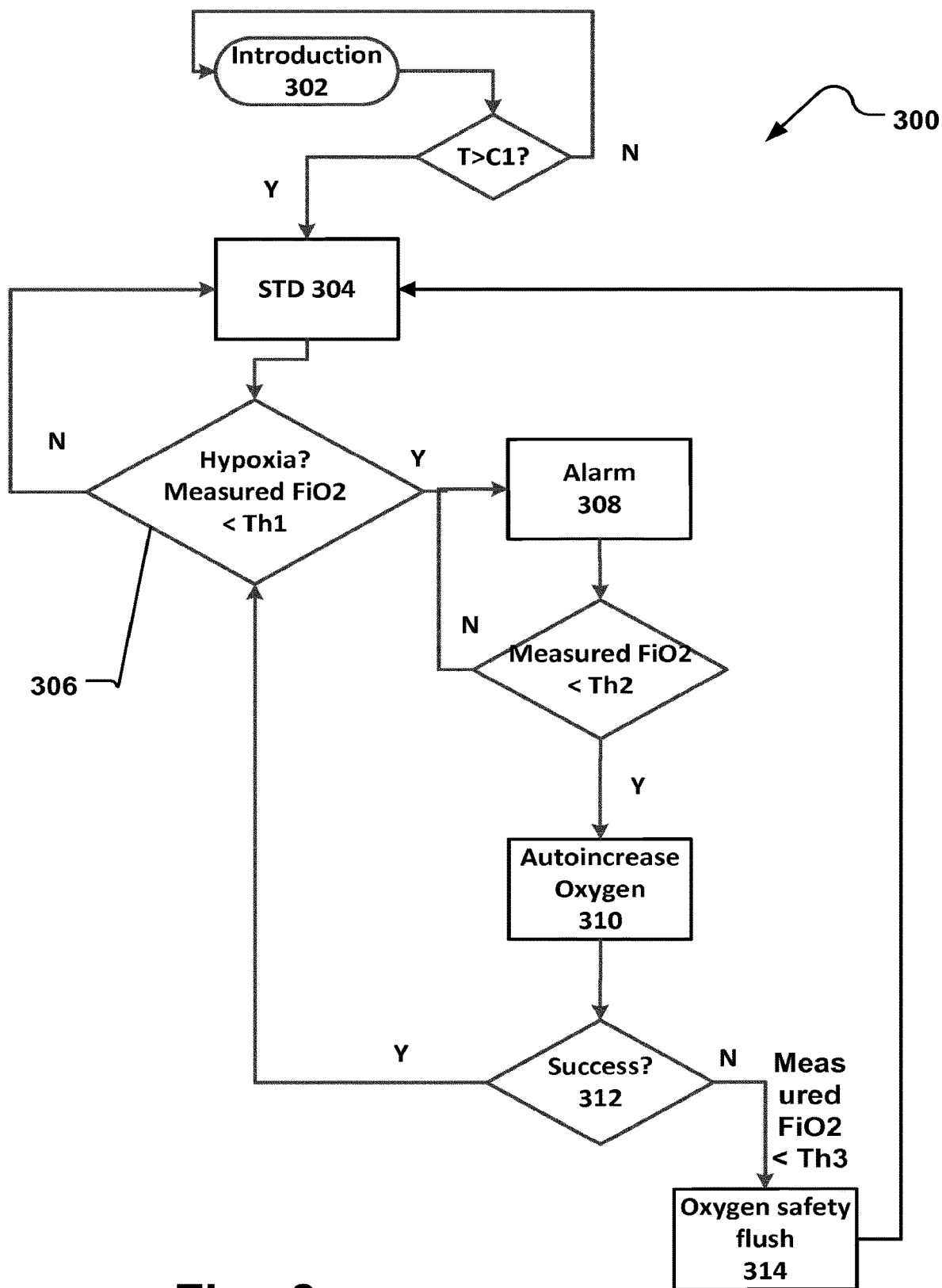
FIG. 3 is a flow chart of safety features of an anesthesia system.
Figure 4:
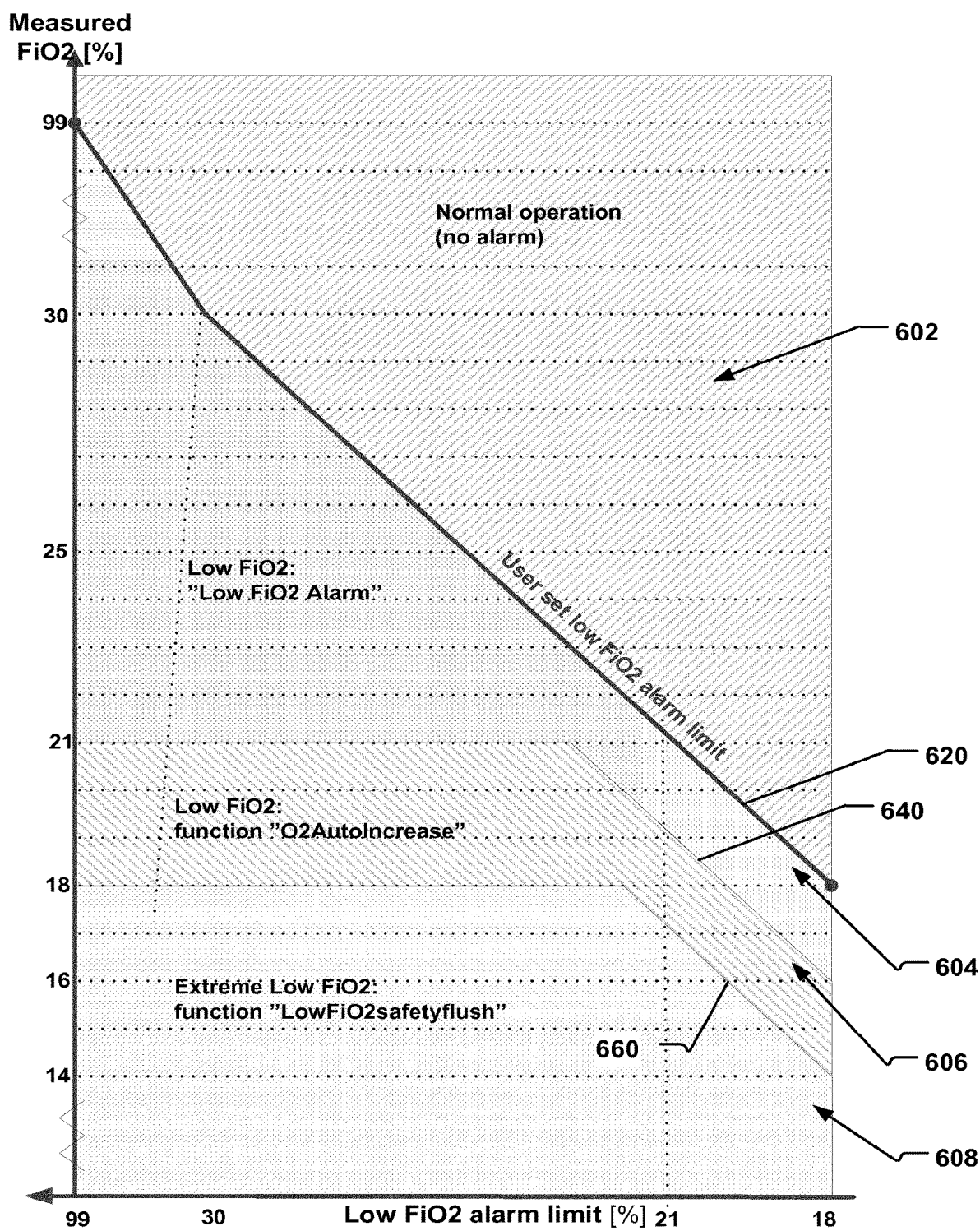
FIG. 4 is a graph illustrating an example of anesthesia system alarms and actions at different delivered oxygen concentrations.

Now turning to FIGS. 3 and 4 an example of an implementation of a Hypoxic Guard is provided. FIG. 3 is a flow chart of an operational method 300 illustrating safety features of an anesthesia system 100. FIG. 4 is a graph illustrating an example of anesthesia system alarms and actions at different delivered oxygen concentrations. FIG. 4 shows an example of FiO2 levels at which different functions of the Hypoxic Guard are triggered. In FIG. 4, Inspiratory oxygen concentration is shown on the Y-axis, and the inspiratory oxygen alarm level is shown on the X-axis.

Initially, the anesthesia system is put in a start-up state 302. The anesthesia system may stay in this introduction or start-up state for a period of time C1.

The anesthesia system proceeds to a normal operational mode 304 in which a patient is mechanically ventilated and provided with inhalational anesthesia. This operational mode of Normal operation (no alarm) is shown in the graph of FIG. 4 in a normal operating area 602.

While the anesthesia system is in this normal operational mode 304, it is regularly checked 306 whether the patient is in risk of entering hypoxia. This check is for instance done in the manner described below with reference to FIG. 4. If the currently measured FiO2 is above a first threshold Th1, the patient is normally ventilated and assumed to be provided with sufficient FiO2. As long as the patient has not entered hypoxia, there is no alarm 308 for hypoxia sent. If the measured inspired oxygen is within the normal operation area 602, labeled "Normal operation (no alarm)", a normal operation is performed, i.e. no alarm is given.

However, if a measured value of inspired oxygen delivered to a patient is below a first threshold value Th1, then an alarm is given to the operator. In FIG. 4, the threshold Th1 is the User set FiO2 alarm limit as illustrated by line 620 delimiting the normal operating area 602 and of a low FiO2 alarm area 604 triggered because the currently measured FiO2 value is below Threshold Th1.

FIG. 4 includes thus further areas, including the low FiO2 alarm area 604 during Activation of a low inspiratory oxygen alarm, a low $FiO_2$ area 606 during Activation of an O2Guard, and an Extreme Low Fi02 area 608 during Activation of a Safety O2 Flush. As long as the Fi02 level is above the threshold Th2, i.e. above a delimiting line 640 in the low Fi02 alarm area 604, only an alarm is given. A Hypoxic guard action is neither necessary nor performed. It should be noted that the thresholds Th2 and Th3 as well as their curvature along the FiO2 alarm limit may be set in a default configuration. Additionally or alternatively, the user may define at least a portion and level of Th2 and/or Th2 as well as their curvature along the FiO2 alarm limit. FIG. 4 is illustrating a preferred example only.

The two "O2 Guard" and "Safety O2 Flush" features will now be described in detail.

Start by noting in the graph in FIG. 4 the value of the User set "low FiO2 alarm limit" on the delimiting line 640 that separates the normal operation area 602 from the low FiO2 alarm area 604. This point is below referred to as "1". From the point in 1 go in a straight vertical line to obtain the limit where the functions "O2autoincrease" (O2 Guard) and "LowFiO2safetyflush" (Safety Oxygen Flush) are triggered.

The low FiO2 alarm area 604 is further delimited to lower FiO2 values by the delimiting line 640. Once the delimiting line 640 is crossed, an operational safety mode may be initiated by the anesthesia system 100, as described below.

If the measured inspired oxygen value FiO2 is within the low FiO2 alarm area 604, labeled "Low Fi02 Alarm: "Low Fi02 Alarm"", an alarm will be given by the anesthesia system 100. As long as the measured value of inspired oxygen delivered to a patient is lower than the first threshold value Th1 but higher than a second threshold value Th2, i.e. values are within the low FiO2 alarm area 604, the alarm will be given only, as illustrated with step 308 in FIG. 3. Interference with a low Oxygen alarm is thus avoided.

If the measured inspired oxygen value FiO2 is within the LowFiO2 area 606, labeled "Low FiO2 Alarm: function "O2AutoIncrease"", a control unit is configured to set the system to an operational safety mode, wherein a safety gas mixture is provided to the patient at a predefined configuration in the safety mode for increasing the oxygen delivered to the patient.

In one embodiment, the "O2autoincrease" function will support the user in order to avoid that hypoxic gas is supplied to the user. Preferably a safety increase of O2 is done a predetermined time after the user is given an opportunity to take suitable counter action. Once the user does not take action in reaction to the O2 alarm, the system acts to increase FiO2.

In some embodiments there exists a user adjustable low FiO2 alarm which notifies the user when the FiO2 is below the set low O2 alarm limit. The user can upon noticing this alarm, adjust the fresh gas settings to avoid a potential harmful situation, where the extreme case is hypoxia. The "O2autoincrease" function is not intended to interfere with that part of the user workflow. The threshold for when the function is activated will always be below the low FiO2 alarm. The function can thus be regarded as an extra safety function in case the user does not take appropriate action(s), for whatever reasons, when the low FiO2 alarm is activated.

When an O2/AIR gas mix is used for fresh gas and the system detects that the FiO2 is below the first threshold Th1, the system will automatically adjust the fresh gas flow and the O2 concentration to predefined levels when the user does not take suitable action in reaction to the triggered alarm, such as within a predetermined time from the alarm being triggered. "O2AutoIncrease" means that more amount of O2 is supplied to the circuit and thereby increasing the FiO2.

When O2/N2O is used for fresh gas and the system detects that the FiO2 is below a certain threshold, the system will change the gas mix to O2/AIR. There will be a user interaction notifying the user that the system has adjusted the fresh gas settings and the system will maintain these settings until the user alters them. Operation of "O2AutoIncrease" implies that more amount of O2 is supplied to the circuit and thereby increasing the FiO2.

Once the system detects that the FiO2 level is below the first threshold Th1, the system may automatically adjust the fresh gas (FG) flow and the O2 concentration to predefined levels when the user does not take suitable action in reaction to the triggered alarm (see e.g. FIG. 5A).

Figure 5A:
FIGS. 5A-5C show a simplified course of actions taken as safety measures in order to prevent hypoxia.
Figure 5B:
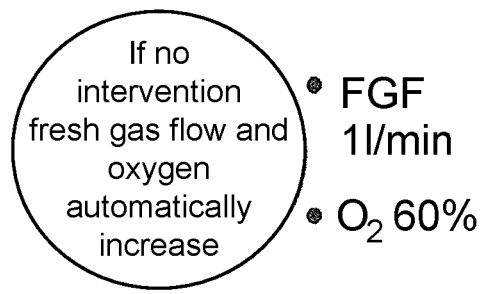

The FG flow (FGF) and/or FG O2 may be increased by a fixed increase from a current FG flow and/or FG O2 level (step increase) or be increased to a predefined FG flow and/or FG O2 level to increase FiO2 (see FIG. 5B). The step may for instance be to a FGF of 1 l/min and/or an FG O2 of 60%. The user is notified of this operative condition, e.g. on a display of the system. The step increase may be maintained until the user interacts with the system to change or stop the FGF and/or FG O2. Alternatively, the increase may be maintained a predefined time only, or until a non-hypoxic FiO2 level is obtained again.

When the measured value of inspired oxygen FiO2 delivered to a patient, goes below the second threshold value Th2, which is lower than the first threshold value Th1, then a control unit is configured to set the system to the operational safety mode. In the operational safety mode, a safety gas mixture is provided in step 310 to the patient at a predefined configuration for increasing the oxygen delivered to the patient. In FIG. 4, the threshold Th2 is illustrated by the delimiting line 640. For such low FiO2 values, the O2AutoIncrease function is initiated, as illustrated by step 310 in FIG. 3, at least after a predetermined time C2 of FiO2 values being below Th2. The O2AutoIncrease function may be initiated at a shorter time than C2, e.g. immediately, in case Fi02 has been below the threshold Th1 for a predetermined time, i.e. the user has been presented with a low O2 alarm for sufficient long time without taking action and the 02 levels reach hypoxic levels. The same applies to triggering of the oxygen safety flush below the third threshold Th3. The predetermined time is for instance about or more than 20 consecutive seconds.

If the measured value of inspired oxygen delivered to a patient, goes below a third threshold Th3, as illustrated in step 312 in FIG. 3, which is lower than the second threshold, then a unit of the anesthesia system 100 automatically performs an oxygen safety flush 314 of a breathing circuit for a predetermined amount of time (see FIG. 5C). A flush may for instance be made with FGF 3 l/min and 100% FG 02.

This "lowFiO2safetyflush", a oxygen safety flush, may be performed directly, without the system entering the safety mode (not shown), if the system has not yet entered the safety mode, when the measured value of inspired oxygen delivered to a patient goes below a third threshold value Th3. If the measured inspired oxygen is within the Extreme Low FiO2 area 608, labeled "Extreme Low FiO2: function LowFiO2safetyflush", the control unit is configured to set the system to automatically perform an oxygen safety flush of the breathing circuit 7 for a predetermined amount of time. The O2 flush may be done during for instance 1-10 seconds, preferably 2-3 seconds.

While the function "O2autoincrease" does comparably small adjustments of the settings to correct a situation indirectly caused by how the user choose settings, the "lowFiO2safetyflush" is a safety action of the system intended to handle more extreme situations like for instance machine failure leading to very low FiO2 levels. It will first perform a safety flush with the intention of exchanging the gas within the system (fresh gas line, patient cassette and gas used for rebreathing) with a gas with high O2 concentration and then increase the fresh gas flow. This flush procedure may be the same as already defined existing flush procedures in the system, but which traditionally are not initiated automatically by the system (as here) but the operator had to manually select the desired flush procedure, e.g. by pushing a dedicated flush button.

The safety flush, when initiated by the control unit of the system, fills and flushes the breathing circuit with preferably 100% O2 gas during the afore mentioned couple of seconds, such as by delivering fresh gas with 100% O2 only to the breathing circuit. This implies a loss of AA to the exhaust, but ensures that the breathing circuit is filled with non-hypoxic O2 concentrations for delivery to the patient. AA can quickly be re-filled to the breathing circuit after this flush procedure, for instance via FG and from a bellows or volume reflector and/or and AA adsorber in the breathing circuit.

One important feature of the function is that it is simple to understand and robust, i.e. it is not activated on false indications, in order not to interfere with the normal workflow of the user. It is of great advantage to let the user be in charge at all times. The system should be polite to the user, but come to the rescue if the user neglects to take appropriate action(s) to avoid harming the patient. For the two exemplary functions included in the Active O2 function this includes that technical issues, such as measured FiO2 signal natural variances or lack of valid values, does not falsely trigger any of the functions. The control unit 60 is configured to avoid false triggering of the Active O2 functions, e.g. when no reading of FiO2 is available or the FiO2 signal is within a range corresponding to the natural variations. Moreover, the system allows enough time for the user to act upon the low FiO2 alarm before the function "O2autoincrease" is activated. The system only activates the safety O2 functions when true risk of harm exist, i.e. triggering levels of thresholds Th2 and Th3 should be close to when a hypoxic gas mix is delivered to the patient.

Figure 5C:
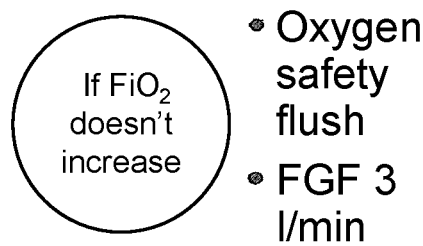

FIGS. 5A-5C show a simplified course of action. The values given are the ones referred to in the example of the graph of FIG. 4. This example may be to illustrate what can happen during Low Flow anesthesia.

A user sets a Low FiO2 alarm limit (Th1) to 18-99%, such as 25%.

The triggering limit (Th2) for the function "O2autoincrease" will be the minimum of a predefined Fi02 value A, e.g. 21% over a certain low Fi02 alarm limit range, or the "low Fi02 alarm" limit minus a value X, such as 2%. The amount of 2% for X is merely an example and other values may be chosen for this offset or "delta" value X. In the example in FIG. 4, this means that the delimiting line 640 between the low Fi02 alarm area 604 and the low $FiO_2$ area 606 follows a fixed value of 21% until a Fi02 alarm limit of 23%. Under 23%, a distance of X, here 2, % is kept for the delimiting line 640 to line 620. See FIG. 5A.

During the function "O2autoincrease", i.e. in the low $FiO_2$ area 606, in some example, a predefined flow and concentration of O2, such as 1 liter of 60% oxygen, is delivered to the patient until the operator sets a new value. See FIG. 5B. The function "O2autoincrease" is entered if the user does no intervention to a present low Fi02 alarm (Fi02<Th1), such as for a predetermined time. The increased value of 02 may be provided during a predefined time, or until a new user setting. If time limited, a new check is done for current Fi02, see FIG. 3 step 312 looping back to step 306.

The limit for the function "LowFiO2safetyflush" (Th3) will be the minimum of a predefined Fi02 value B, e.g. 18% over a certain low Fi02 alarm limit range, or the "O2autoincrease" limit minus a value Y, such as 2%. The amount of 2% for Y is merely an example and other values may be chosen for this "delta" value Y. In the example in FIG. 4, this means that the delimiting line 660 between areas the low $FiO_2$ area 606 and the Extreme Low FiO2 area 608 follows a fixed value of 18% until a FiO2 alarm limit of 22% (=B+X+Y %, here 18+2+2%). Under 22%, a distance of Y, here 2, % is kept for the delimiting line 660 to the delimiting line 640.

The function "LowFiO2safetyflush" delivers in some embodiments 100% oxygen and thus, the system will respond with a step response. For instance, if FiO2 does not increase despite the increased O2 provided by the function "O2autoincrease", a FG flow of 3 l/min and 100% O2 may be provided to the breathing circuit for an Oxygen safety flush. See FIG. 5C.

The function "O2autoincrease" may be selected to be only enabled when the function is enabled in service and settings of the anesthesia system 100, i.e. the function "O2autoincrease" can be disabled.

Low Flow anesthesia typically has settings such as FLOW=0.4 l/min and O2 concentration=50%.

Suitable values for low FiO2 alarm limits, hypoxia limits for delimiting areas 602 (normal operating area), 604 (the low FiO2 alarm area), 606 (the low FiO2 area), and 608 (the Extreme Low FiO2), for specific patients or specific patient categories, may be chosen from look-up tables according to patient weight, length etc.

The measured inspired oxygen may be measured at the Y-piece or the fresh gas line or any other suitable sampling place in anesthesia system 100.

When the Hypoxic Guard functions are activated, the user is preferably informed that fresh gas settings have been altered accordingly and that these settings will be maintained until the user alters them. Different dialogues may be used within the Hypoxic Guard function. One dialogue may be provided to the user for the "O2autoincrease" function, i.e. when the measured inspired oxygen is within the low FiO2 area 606, labeled "Low FiO2 function O2Autoincrease", and the disabling of the O2/N20 gas mix when such mixture was used before the normal operating area 602 was entered. The dialogue may be overridden by a Safety Flush-dialogue when area the Extreme Low FiO2 608 is entered.

Thus, there is also one dialogue for the "LowFiO2safetyflush", i.e. when the measured inspired oxygen is within the area 608, labeled "Extreme Low FiO2 function LowFiO2safetyflush" of FIG. 4.

The user may de-activate the Hypoxic Guard function, e.g. during an induction phase when low FiO2 situations may be present until a stable ventilation of the patient is obtained in the normal operational mode.

Figure 6:
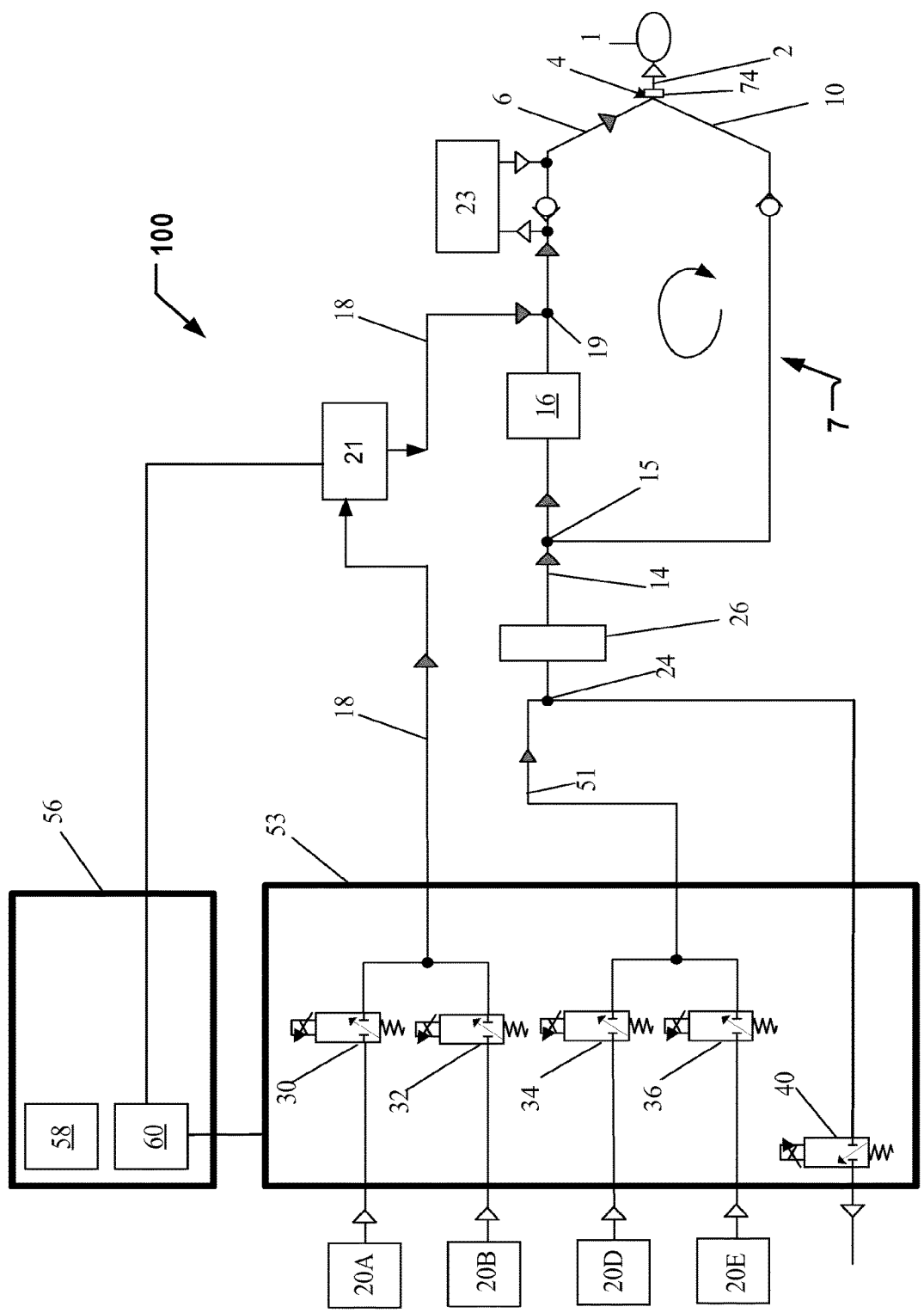
FIG. 6 is a schematic illustration of an example of an anesthetic breathing apparatus having an anesthetic reflector unit, in an inspiration phase.

FIG. 6 illustrates an example of the anesthesia system 100 of FIG. 1 in more detail. The Hypoxic Guard function is implemented in the example. FIG. 6 shows schematically, a breathing circuit of an anesthetic breathing apparatus, coupled to a circle system 7 with a mechanical ventilation system 53. The airways of a patient 1 are connected to a patient tube 2 of a Y-piece 4 in a circular tubing system with an inspiration and expiration tube 6, 10. A patient gas sensor 74 including FiO2 value measurement capability, is provided in the patient tube 2 connected to the Y-piece 4. Downstream the Y-piece 4, in FIG. 6 in a clockwise direction along the circle system 7, a common expiration and inspiration line 14 is provided for bidirectional flow to and from the patient. The common expiration and inspiration line 14 is coupled to the circle system 7 at a first junction 15. Further along the circle system 7, the tubing passes through a carbon dioxide CO2 absorber 16. Downstream the CO2 absorber 16, a fresh gas (FG) supply branch line 18 is provided to feed gas into the circle system 7 from a gas source. The fresh gas supply branch line 18 has a proximal portion in which fresh gas is supplied to an anesthetic vaporizer 21. The fresh gas is further conveyed via a distal portion of the fresh gas supply branch line 18, as desired enriched with gaseous anesthetic agent by the anesthetic vaporizer 21. The fresh gas supply branch line 18 is distally coupled to the circle system 7 at a second junction 19.

The common expiration and inspiration line 14 is provided with a volume reflector unit 26.

The fresh gas inhalation source may comprise multiple gas sources, such as an oxygen gas source 20A, and an air gas source 20B, as illustrated in FIG. 6. Additionally, the fresh inhalation gas source may comprise a nitrous oxide gas source (not shown). The anesthetic vaporizer 21 is fluidly connected to the fresh gas supply branch line 18 downstream gas sources 20A, B and upstream the second junction 19. A gas analyzer 23 may be provided to analyze gas contents with an input of sample inspiratory gas including FiO2 in a side stream configuration. The patient gas sensor 74 may be dispensed with, when gas analyzer 23 is present, but might give a more accurate FiO2 value. The terms upstream and downstream used herein are as seen during an operational inspiration phase of the breathing apparatus, as shown in FIG. 6.

At the side turned opposite the circle system 7, the volume reflector 26 of the common expiration and inspiration line 14 is coupled at a third junction 24 to a reflector driving gas line 51 for pushing reflector driving gas into the proximal end of the volume reflector. Thus, gas may be pushed out of the distal end of the volume reflector into the common expiration and inspiration line 14 downstream the volume reflector 26 and into the circle system 7.

A ventilation control system 56 may comprise a user interface 58 with command input means and display means. The user interface may be provided for user adjustments of the Hypoxic Guard settings, or status indications of the current operational mode. The ventilation control system 56 further comprises a control unit 60, amongst others to control the anesthetic vaporizer 21 and operation of the mechanical ventilation system 53.

The control unit 60 enables vent of breathing gas from the mechanical ventilation system according to a set of predetermined control rules for controlling the expiratory valve 40 in accordance with ventilation mode requirements. The expiratory valve 40 is usually closed during inspiration and controls the expiratory pressure level, and expiratory flow, during expiration.

The control unit 60 is configured to provide the Hypoxic Guard function described in detail above in the anesthesia system 100.

The breathing apparatus comprises in addition to the fresh gas inhalation source further gas sources, such as an oxygen gas source 20D, and an air gas source 20E, as illustrated in FIG. 6. The further gas source provides a reflector driving gas (RDG). A first inspiratory valve 34 and a second inspiratory valve 36 are controlled to provide a desired oxygen concentration, nitrous oxide may also be used, in a gas flow to the reflector driving gas line 51.

Gas sources 20A, B are coupled to a third inspiratory valve 30 and a fourth inspiratory valve 32, connected to the fresh gas supply branch line 18. During inhalation, a gas flow ratio may thus be controlled, by control unit 60, between a gas flow crated in the fresh gas supply branch line 18 and a gas flow created the line 14 in order to adjust a degree of rebreathing gas being pushed from volume reflector 26 via line 14 into the circle system 7. A measure for gas flow via the fresh gas supply branch line 18 is provided by suitable gas flow sensors. For instance oxygen gas sources 20A, 20D and/or air gas sources 20B, 20E may have integrated flow meters.

The distribution of the amounts of gas flow between the fresh gas supply branch line 18 and the reflector driving gas line 51 is adjustable in real time by control unit 60. The flow delivered to the patient during inspiration is thus defined by the sum of gas provided by the reflector driving gas line 51 and the fresh gas supply branch line 18. Thus, a desired re-breathing fraction (RBF) is adjustable by controlling the inspiratory valves 20A,B,D and E.

The gas pushed from the volume reflector and/or adsorption filter 26 into the circle system 7 is composed of previously exhaled patient gas, e.g. including one or more anesthetic agents. Hence, this previously exhaled patient gas is provided for re-breathing to the patient, after passing through the CO2 absorber 16. In a low flow operational mode (i.e. the highest possible RBF), the breathing apparatus may be controlled in such a manner that only the anesthetic agent and oxygen consumed by the patient is re-added to the circle system 7. In case too little oxygen is admixed to the circle system 7, the patient may subject to hypoxia, which is undesired. The Hypoxic Guard as described herein effectively counteracts the patient to become hypoxic.

The anesthesia system 100 is thus provided with a hypoxic guard system, such as described above with reference to FIGS. 3 and 4. The anesthesia system 100 comprises the patient gas sensor 74 for measuring inspired oxygen delivered to the patient 1 fluidly connected to the anesthesia system 100. The anesthesia system 100 also comprises a control unit 60 for triggering an alarm if the measured inspired oxygen F102 is below a first threshold value Th1. The control unit 60 is configured to set the system 100 to a safety mode if the measured inspired oxygen FiO2 is below a second threshold value Th2. The second threshold value Th2 is lower than the first threshold value Th1. A safety gas mixture is provided to the patient at a predefined configuration in the safety mode for increasing the oxygen delivered to the patient 1. The control unit 60 is thus configured to set the system to an operational safety mode for increasing the delivery of oxygen to the patient 1 in such case. The control unit 60 is further configured to activate the operational safety mode if the measured inspired oxygen value is below the first and/or second threshold value Th1, Th2 for at least a first predetermined time for mitigating or avoiding hypoxia of the patient.

The control unit 60 may further be configured to set the anesthesia system 100, for automatically performing an oxygen flush, such as of the circle system 7 of the anesthesia system 100. The oxygen flush is performed for a predetermined amount of time if the measured inspired oxygen value is below a third threshold value Th3, preferably for at least a second predetermined time, wherein the third threshold is lower than the second threshold value.

Figure 7:
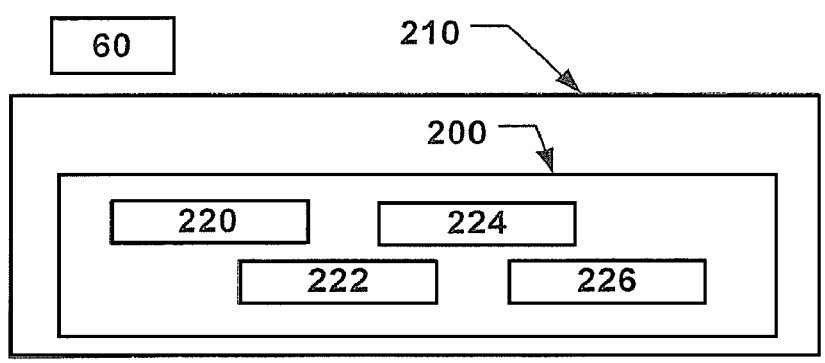
FIG. 7 is a schematic illustration of a computer readable medium.

As illustrated in FIG. 7, a computer-readable 210 medium may be provided having embodied thereon a computer program 200 for processing by a computer, such as control unit 60 of the anesthesia system 100. The computer program 200 comprises a first code segment 220 for measuring inspired oxygen delivered to a patient fluidly connected to the anesthesia system 100. The computer program further comprises a second code segment 222 for triggering an alarm if the measured inspired oxygen is below a first threshold value. Moreover, the computer program 200 comprises a third code 224 segment for setting the system to a safety mode if the measured inspired oxygen is below a second threshold value lower than the first threshold, wherein a safety gas mixture is provided to the patient at a predefined configuration in the safety mode for increasing the oxygen delivered to the patient. The system is set to the operational safety mode for increasing delivery of said oxygen to said patient when said measured inspired oxygen value is below a second threshold value lower than said first threshold value for at least a first predetermined time.

The computer program may include a fourth code segment 226 for setting the anesthesia system 100 in an operational mode automatically performing an oxygen flush, such as of a breathing circuit of the system. The oxygen flush is performed for a predetermined amount of time if the measured inspired oxygen value is below a third threshold value for at least a second predetermined time, wherein the third threshold is lower than the second threshold value.

Hence, if the anesthesia system 100 detects an inspiratory oxygen concentration below a certain level Th1, Th2 or Th3, it initiates actions to mitigate an adverse situation. The gas mix is set to Air/O2, the fresh gas flow and oxygen concentration are both adjusted. A dialog window appears informing of the alterations. These changes remain in effect until new settings are made.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

We claim as our invention:

1. An anesthesia system, comprising:
a unit providing a measured inspired oxygen value (FiO2) for oxygen delivered to a patient fluidly connected to said system; and
a control unit triggering an alarm action in said system for an inspiratory oxygen alarm if said measured inspired oxygen value (FiO2) is below a first threshold value and above a second threshold value that is lower than the first threshold value; and wherein
said control unit is configured to set said system to an operational safety mode for increasing delivery of oxygen to said patient, and wherein said control unit is configured to activate said operational safety mode if said measured inspired oxygen value (FiO2) is below the second threshold value.

2. The anesthesia system of claim 1, wherein said control unit is configured to activate said operational safety mode when said measured inspired oxygen value (FiO2) has been lower than said first threshold value for at least a first predetermined time and/or an inspiratory oxygen alarm or warning has been presented to a user of said system.

3. The anesthesia system of claim 1, wherein said control unit is configured to switch to fresh gas sources for O2 and air when O2 and N2O are used as fresh gas sources in the system and FiO2 is below the second threshold, wherein said control unit is configured to provide a user notification that the system has adjusted the fresh gas settings and the system maintains these settings until the user alters them.

4. The anesthesia system of claim 1, wherein said control unit is configured to perform an oxygen flush of a breathing circuit of said system for a predetermined amount of time if said measured inspired oxygen value is below a third threshold value, for at least a second predetermined time, said third threshold being lower than said second threshold value.

5. The anesthesia system of claim 4, wherein said control unit is configured to set said system to said operational safety mode only if the user is non-responsive to warnings or alarms indicating a low FiO2 condition, between the first and second threshold values, or between the second and third threshold values, or below the third threshold values, before increased, non-hypoxic, O2 amount is delivered to the patient to mitigate or avoid hypoxia.

6. The anesthesia system of any of claim 4, wherein any of the first, second or third threshold values are user settable within a predeteiinined or settable range.

7. The anesthesia system of claim 1, wherein said control unit is configured to provide a fixed oxygen amount to said patient in said operational safety mode.

8. The anesthesia system of claim 1, wherein said control unit is configured to increase said delivered oxygen by controlling a composition and/or flow of a fresh gas provided to a breathing circuit of said system.

9. The anesthesia system of claim 8, wherein said fresh gas composition to be delivered in said operational safety mode is selectable by an operator of said system.

10. The anesthesia system of claim 1, wherein said control unit is configured to activate said operational safety mode if said measured inspired oxygen value (FiO2) is below the second threshold value and has been below the first threshold value for a predetermined amount of time or has been below the second threshold value for a predetermined amount of time.

11. A method mitigating or avoiding hypoxia of a patient fluidly connected to an anesthesia system, said method comprising:
providing a measured inspired oxygen value for oxygen delivered to said patient;
triggering an alarm action in said system if said measured inspired oxygen value is below a first threshold value and above a second threshold value that is lower than the first threshold value; and
setting said system to an operational safety mode for increasing delivery of said oxygen to said patient when said measured inspired oxygen value is below the second threshold value for at least a first predetermined time.

12. The method of claim 11, including activating said operational safety mode when said measured inspired oxygen value (FiO2) has been lower than said first threshold value for at least a first predetermined time and/or an inspiratory oxygen alarm or warning has been presented to a user of said system.

13. The method of claim 11, including switching to fresh gas sources for O2 and air when O2 and N2O are used as fresh gas sources in the system and FiO2 is below the second threshold, and preferably providing a user notification that the system has adjusted the fresh gas settings and the system maintains these settings until the user alters them.

14. The method of claim 11, including performing an oxygen flush of a breathing circuit of said system for a predetermined amount of time if said measured inspired oxygen value is below a third threshold value for at least a second predetermined time, said third threshold being lower than said second threshold value.

15. The method of claim 14, wherein setting said system to said operational safety mode is done only if the user is non-responsive to warnings or alarms indicating a low FiO2 condition, between the first and second threshold values, or between the second and third threshold values, or below the third threshold values, before increased, non-hypoxic, O2 amount is delivered to the patient to mitigate or avoid hypoxia.

16. The method of claim 14, wherein any of the first, second or third threshold values are user settable within a predetermined or settable range.

17. The method of claim 11, wherein said increasing delivery of said oxygen includes providing a fixed oxygen amount to said patient in said operational safety mode.

18. The method of claim 11, wherein said increasing delivery of said oxygen is provided by controlling a composition of a fresh gas provided to a breathing circuit of said system.

19. The method of claim 18, including providing said fresh gas composition to be delivered in said operational safety mode as selectable by an operator of said system.

20. A non-transitory, computer-readable data storage medium encoded with programming instructions, said storage medium being loaded into a control computer of an anesthesia system, and said programming instructions causing said control computer to:
receive a measured inspired oxygen value for oxygen delivered to the patient by said anesthesia system;
trigger an alarm action in said anesthesia system if said measured inspired oxygen value is below a first threshold value and above a second threshold value that is lower than the first threshold value; and
set said system to an operational safety mode for increasing delivery of said oxygen to said patient when said measured inspired oxygen value is below the second threshold value for at least a predetermined time duration.

* * * * *